United States Patent
Xiao et al.

(10) Patent No.: US 11,771,656 B2
(45) Date of Patent: Oct. 3, 2023

(54) ORAL COLON-TARGETED DELIVERY SYSTEM AND PREPARATION METHOD AND APPLICATION THEREOF

(71) Applicant: Shanghai Jiaotong University School of Medicine, Shanghai (CN)

(72) Inventors: Zeyu Xiao, Shanghai (CN); Lei Lu, Shanghai (CN); Gaoxian Chen, Shanghai (CN); Miao Lin, Shanghai (CN)

(73) Assignee: Shanghai Jiaotong University School of Medicine, Shanghai (CN)

( * ) Notice: Subject to any disclaimer, the term of this patent is extended or adjusted under 35 U.S.C. 154(b) by 277 days.

(21) Appl. No.: 16/461,564

(22) PCT Filed: Nov. 17, 2016

(86) PCT No.: PCT/CN2016/106175
§ 371 (c)(1),
(2) Date: Jan. 15, 2020

(87) PCT Pub. No.: WO2018/090266
PCT Pub. Date: May 24, 2018

(65) Prior Publication Data
US 2020/0206141 A1    Jul. 2, 2020

(51) Int. Cl.
| | | |
|---|---|---|
| *A61K 9/48* | (2006.01) | |
| *A61K 9/16* | (2006.01) | |
| *A61K 47/36* | (2006.01) | |
| *A61K 47/40* | (2006.01) | |
| *A61K 47/42* | (2017.01) | |
| *A61K 47/46* | (2006.01) | |
| *A61K 47/68* | (2017.01) | |
| *A61K 47/69* | (2017.01) | |

(52) U.S. Cl.
CPC .............. *A61K 9/4891* (2013.01); *A61K 9/16* (2013.01); *A61K 47/36* (2013.01); *A61K 47/40* (2013.01); *A61K 47/42* (2013.01); *A61K 47/46* (2013.01); *A61K 47/6843* (2017.08)

(58) Field of Classification Search
CPC ........ A61K 9/4891; A61K 9/16; A61K 47/36; A61K 47/40; A61K 47/42; A61K 47/46; A61K 47/6843; A61K 47/6937
See application file for complete search history.

(56) References Cited

U.S. PATENT DOCUMENTS

| | | | | |
|---|---|---|---|---|
| 6,231,888 | B1 * | 5/2001 | Lerner ................. | A61K 9/2027 424/463 |
| 2010/0303723 | A1 * | 12/2010 | Farokhzad ............ | A61K 47/68 424/9.1 |
| 2013/0273137 | A1 * | 10/2013 | Mandell ................. | A61L 27/28 424/428 |
| 2015/0147270 | A1 * | 5/2015 | Merlin ................. | A61K 31/713 424/1.11 |

FOREIGN PATENT DOCUMENTS

| | | | |
|---|---|---|---|
| CN | 105832691 | * | 8/2016 |
| CN | 105832691 A | * | 8/2016 |
| WO | WO 2008059062 | * | 5/2008 |

OTHER PUBLICATIONS

Xiao et al, Combination therapy for ulcerative colitis: orally targeted nanoparticles prevent mucosal damage and relive inflammation. Theranostics, 2016, vol. 6, Issue 12. (Year: 2016).*

Chourasia et al, Polysaccharides for colon targeted drug delivery, Drug delivery 11:129-148. (Year: 2004).*

* cited by examiner

*Primary Examiner* — Mina Haghighatian
(74) *Attorney, Agent, or Firm* — Ice Miller LLP (57) ABSTRACT

An oral colon-targeted delivery system is described, which includes a bacterial flora sensitive layer which contains polysaccharides and covers the exterior of active ingredients, a pH sensitive layer which contains any polymer composition dissolved under the condition of pH≥7 and covers the exterior of the bacterial flora sensitive layer. A preparation method and applications of the delivery system are also described. According to the oral colon-targeted delivery system combined with the pH sensitive and bacterial flora sensitive mechanisms, the selective dissolution and release of active ingredients in the colon site are effectively improved by using double-layer protection so that the therapeutic or diagnostic effect is enhanced, and the application prospect is broad.

8 Claims, 5 Drawing Sheets

ORAL COLON-TARGETED DELIVERY SYSTEM AND PREPARATION METHOD AND APPLICATION THEREOF

CROSS-REFERENCE TO RELATED APPLICATIONS

This application is a Section 371 of International Application No. PCT/CN2016/106175, filed Nov. 17, 2016, which was published in the Chinese language on May 24, 2018, under International Publication No. WO 2018/090266 A1, the disclosure of all of which is incorporated herein by reference in its entirety.

FIELD

The present invention relates to the field of medical technology, in particular to a new oral colon-targeted delivery system, preparation method and application thereof. The delivery system can obtain ideal selective targeting of colon and has a good application value for diagnosis and treatment of colonic diseases.

BACKGROUND

At present, colonic diseases, such as: colon cancer and inflammatory enteritis, are threatening human health. The statistical results of cancer mortality rates in 2015 show that: the number of colorectal cancer cases in the world is 1.02 million, ranking third among all fatal cancers. 177,000 of them are Chinese patients, ranking fourth among all the countries. The distribution statistics of the incidence of inflammatory enteritis show that there is a high incidence in Western countries, the number of cases in China is gradually increased with the changes in environment and living habits, and the incidence of inflammatory enteritis is rising year by year at an alarming rate worldwide. This will pose a great threat to the health of all mankind, so it will be of great significance to design relevant methods for treatment.

Currently, there are mainly three drug delivery systems for treatment of diseases in the colon site: single pH-dependent colon-targeted drug delivery system, time-dependent colon-targeted drug delivery system or colon-targeted drug delivery system triggered by bacterial flora/enzyme as detailed below: (1) The PH-dependent targeted drug delivery system is a more common targeted drug delivery system which uses a certain pH-sensitive polymer as a coating for drug encapsulation by taking advantage of the fact that the pH value of the colon site is higher than that of the small intestine so that the coating is dissolved under the pH condition of the colon site and a large quantity of drugs are released. For example: acrylic resin copolymers, cellulose phthalate acetate and the like, wherein EUDRAGIT®S100 is an anionic copolymer based on methacrylic acid and methyl methacrylate. EUDRAGIT®S100 is dissolved at pH≥7 so that drugs are protected in the stomach from damage by the acidic environment and do not release their active ingredients until they reach the intestinal tract. (2) The time-dependent colon-targeted drug delivery system refers to drug release after activities in the gastrointestinal tract for a longer time due to the time difference produced by the swelling capacity of biomaterials to achieve the purpose of intestinal targeting. The time lag is mainly regulated and controlled by particle size, coating thickness and permeability to the colon site, but the system is greatly affected by individual differences, food categories, eating time, pathological conditions and other factors. (3) The colon-targeted drug delivery system triggered by bacterial flora/enzyme is based on the fact that the concentration of bacterial floras in the colon site increases sharply compared with that in the stomach and small intestine. These bacterial floras can secrete many specific reductases and hydrolases, such as β-glucuronidase, β-glucosidase, cellulase, nitroreductase, azo reductase, α-decarboxylase, cholesterol dehydrogenase and the like, while azo polymers, polysaccharides and other materials can be degraded by colon-specific enzymes, and the colon targeting preparation triggered by bacterial flora is designed for this reason. For example, chitosan is a natural polysaccharide in which 1,4-glycosidic bonds make it not degradable and absorbable in the stomach and small intestine but degradable under the action of enzymes produced by specific bacteria at the colon. It is a good carrier material for colon-targeted drug delivery system since it is highly targeted, safe, stable, non-toxic and biodegradable.

However, the gastrointestinal environment is complex, the pH has a broad variation range, the length of gastrointestinal tract varies, and individual differences exist. The oral colon delivery system currently reported has the disadvantages that: Single pH-dependent or time-dependent delivery of colon drugs can not guarantee complete arrival at the colon site due to individual differences. Drugs are usually released in advance in the middle and lower ends of the small intestine so that the drugs are absorbed or decomposed in advance, resulting in fewer doses to the colon site, thus a higher initial dose or repeated administration is required, which leads to serious systemic side effects. Most of the materials used by a single bacterial flora sensitive mechanism are compounds in an azo-containing structure and polysaccharides, and the compounds in an azo-containing structure have more significant colon targeting. However, a small molecular azo compound is a strong carcinogen, while polysaccharides are extremely easy to absorb water and swell due to good water absorption so that drugs are released in advance.

SUMMARY OF THE INVENTION

The technical problem to be solved by the present invention is to provide an oral colon-targeted delivery system which combines pH sensitive and bacterial flora sensitive mechanisms, effectively enhances the selective dissolution and release at the colon site by using double-layer protection, enhances the therapeutic or diagnostic imaging effect and reduces toxic side effects.

Additionally, a preparation method and application of the oral colon-targeted delivery system also need to be provided.

In order to solve the above technical problem, the present invention is realized by the technical scheme as follows:

In one aspect of the present invention, an oral colon-targeted delivery system is provided, comprising:

A bacterial flora sensitive layer, which contains polysaccharides and covers the exterior of active ingredients;

A pH sensitive layer, which contains any polymer composition dissolved under the condition of pH≥7 and covers the exterior of the bacterial flora sensitive layer.

The polysaccharides comprise β-cyclodextrin derivative and/or plant extracts and derivatives thereof.

The polymer compositions of the pH sensitive layer comprise components of the following weight percentages: 10%~43% of methacrylic acid-methyl methacrylate copolymer, 5%~36% of plasticizer and 5%~22% of talcum powder.

In the present invention, the term "cover" comprises coating for solid carriers and capsules or microcapsules which encapsulate fluids and/or solids.

In the present invention, the term "active ingredient" refers to any compound or biomaterial useful for diagnosis and/or treatment of diseases.

The outer layer of the delivery system of the present invention is a pH sensitive layer material which can resist the acid environment at the middle and upper ends of the stomach and small intestine because it is dissolved only at pH≥7; the bacterial flora sensitive material in the middle layer can only be dissolved when triggered by the bacterial flora specific to the colon site so that the selective delivery capability of the delivery system to the colon site can be effectively enhanced; the inner layer comprises the active ingredients, comprising drugs or diagnostic reagents, wherein the drugs comprise antibody drugs, protein drugs, gene drugs, nanodrugs, small molecule drugs and the like; the diagnostic reagents comprise contrast agents, imaging probes and other imaging reagents for the diagnosis of inflammatory bowel disease or colon cancer.

Preferably, the drugs are in a targeted nanoparticle dosage form.

Drugs with targeted nanoparticles enter cells under the action of cell uptake by combining modified targeting molecules on the surfaces of the nanoparticles with specific receptors on the surfaces of the cells to achieve safe and effective targeted drug therapy.

More preferably, the targeted nanoparticles are PLGA-PEG nanoparticles modified by CD-98 antibody.

The CD-98 antibody-modified targeted nanoparticles of the present invention can be specifically identified and enriched at the inflammatory site of the colon, stay for a long-lasting effect and release drugs slowly so that the duration of action of the drugs is prolonged, the therapeutic effect of the drugs is improved, thus effectively solving the technical problem that drugs cannot stay at the inflammatory site or achieve the therapeutic effect because small molecule drugs are quickly brought out of the human body with chyme or feces after reaching the colon site in the treatment of diffuse colitis.

The bacterial flora sensitive layer material β-cyclodextrin derivative of the present invention is preferably β-cyclodextrin polymer crosslinked with epichlorohydrin. Options for the bacterial flora sensitive layer material are natural plant extracts such as celery extract, konjac gum or pectin and the like, or derivatives of the natural plant extracts. Other options for the bacterial flora sensitive layer material of the present invention are β-cyclodextrin derivatives, plant extracts and mixture of derivatives thereof.

For the methacrylic acid-methyl methacrylate copolymer in the pH sensitive layer material of the present invention, the preferred ratio of methacrylic acid to methyl methacrylate is 1:2.

The plasticizer in the pH sensitive layer material of the present invention can be selected from methyl or ethyl esters, organic acid fatty esters or inorganic acid esters (such as lactic acid, citric acid, succinic acid, adipic acid, sebacic acid, phthalic acid, glutaric acid or phosphoric acid), or selected from acetate esters or fatty esters of monohydric, dihydric, trihydric or polyhydric alcohols. Specifically, the plasticizer can be selected from glycerol diacetate (glycerol diacetate), glycerin triacetate (triacetin), or triethyl citrate, and any mixture of the products. The preferred plasticizer is triethyl citrate.

The oral colon-targeted delivery system of the present invention can be made into any dosage form, comprising capsules, microcapsules, tablets, pills or granules.

The preparation method of the oral colon-targeted delivery system of the capsule dosage form comprises the following steps:

Dissolve the polysaccharides in an organic solvent, draw a proper amount of the solution, add into a capsule shell, dry at 45~65° C. for 5~15 hours, then cool to room temperature, and obtain the bacterial flora sensitive layer;

Prepare a coating fluid of the pH sensitive layer by mixing the polymer compositions dissolved under the condition of pH≥7, spray on the outer surface of the capsule shell containing the bacterial flora sensitive layer, and obtain the oral colon-targeted delivery system sensitive to both pH and bacterial flora after drying.

In another aspect of the present invention, the application of the oral colon-targeted delivery system in the preparation of drugs for treatment of colonic diseases is also provided.

In another aspect of the present invention, the application of the oral colon-targeted delivery system in the preparation of reagents for diagnosis of colonic diseases is also provided.

In another aspect of the present invention, the application of the oral colon-targeted delivery system in the preparation of drugs for diagnosis and treatment of colonic diseases is also provided.

In another aspect of the present invention, the application of the oral colon-targeted delivery system in the preparation of drugs absorbed orally by the colon is also provided.

The colonic diseases comprise colon cancer, inflammatory colitis, intestinal amebiasis or intestinal tuberculosis.

The oral colon-targeted delivery system of the present invention combined with the pH sensitive and bacterial flora sensitive mechanisms effectively enhances selective dissolution and release at the colon site by using double-layer protection so that the drugs at the inner layer are not released until reaching the colon site, the number of times of administration is reduced, the toxic and side effects are reduced, better therapeutic effects are achieved, and the oral colon-targeted delivery system has broad application prospects.

BRIEF DESCRIPTION OF THE DRAWINGS

The present invention is described in further detail below in combination with the drawings and the description of the preferred embodiments.

DETAILED DESCRIPTION OF THE PREFERRED EMBODIMENTS

In order to solve the technical problem that the current single pH mechanism for delivering colon drugs often results in too little dosage reaching the colon site and the single bacterial flora triggered colon-targeted drug delivery easily leads to swelling after long-time action in the stomach and small intestine since it makes the bacterial flora sensitive layer material highly hydrophilic, which is adverse to normal onset at the colon site, the present invention develops an oral colon-targeted delivery system, comprising: a bacterial flora sensitive layer which contains polysaccharides and covers the exterior of active ingredients; a pH sensitive layer which contains any polymer composition dissolved under the condition of pH≥7 and covers the exterior of the bacterial flora sensitive layer, wherein the active ingredients comprise drugs or diagnostic imaging reagents.

The polysaccharides comprise β-cyclodextrin derivatives and/or plant extracts and derivatives thereof.

The polymer compositions of the pH sensitive layer contain components of the following weight percentages: 10%~43% of methacrylic acid-methyl methacrylate copolymer, 5%~36% of plasticizer and 5%~22% of talcum powder.

Preferably, the drugs are in a targeted nanoparticle dosage form. In one preferred embodiment of the present invention described below, the targeted nanoparticles are PLGA-PEG nanoparticles modified by CD-98 antibody. The CD-98 antibody-modified targeted nanoparticles can be specifically identified and enriched at the inflammatory site of the colon, stay for a long-lasting effect and release drugs slowly so that the duration of action of the drugs is prolonged, and the therapeutic effect of the drugs is improved. This is of great significance for the current treatment of diffuse colitis. Since the existing small molecule drugs in common dosage form are quickly brought out of the human body with chyme or feces after reaching the colon site, the drugs cannot stay at the inflammatory site or play the due therapeutic effect. The pH and bacterial flora sensitive delivery system combined with the targeted nanoparticles can achieve long-acting stay at the site of colonic disease and slow release of drugs and give full play to the efficacy of drugs because the pH and bacterial flora sensitive delivery system can ensure that the targeted nanoparticles are fully delivered to the site of colon disease, and the targeted nanoparticles can specifically identify cells at the site of colonic disease and enter the cells by endocytosis without being eliminated from the body quickly with chyme or feces peristalsis.

The present invention is elaborated below through specific embodiments.

Embodiment 1 Preparation of Oral Colon-Targeted Delivery System

1. Preparation of pH Sensitive Layer

Use 20%±10% Eudragit S100 (RohmGmbH) and 15%±10% triethyl citrate (Sigma-Aldrich) as plasticizers and 5%±10% talc powder (Sigma-Aldrich) as antisticking agent, add the three components into ethanol to form the coating fluid of the pH sensitive layer, stir (Ningbo Scientz Biotechnology Co., Ltd., China) and mix evenly. Spray on the capsule evenly at 45±10° C. through a BY-300A small coating pan (Shanghai Huanghai Drug Inspection Instrument Co.). After drying, it becomes the pH sensitive layer film on the outer layer of the capsule and is dissolved only at pH≥7 so that the capsule can resist the acid environment at the middle and upper ends of the stomach and small intestine.

2. Preparation of Bacterial Flora Sensitive Layer

Dissolve 1.8±1 g β-cyclodextrin polymer crosslinked with epichlorohydrin(β-CDP) (Binzhou Zhiyuan Biotechnology, China) or plant fiber extract in 8±5 ml dimethyl sulfoxide (DMSO) (Sinopharm Group, China). Draw 8±5 ul of the solution, add into a mould gelatin capsule shell made by 3D printing, then dry for 10±5 h at 55±10° C. After cooling to room temperature, the capsule intermediate layer sensitive to bacterial flora in colon is obtained. The capsule intermediate layer can only be dissolved when triggered by the bacterial flora specific to the colon site, so that the selectivity to the colon site can be effectively enhanced. After clamping the capsule shell sensitive to colon bacterial flora vertically, coat the pH sensitive layer for the outer layer of the capsule according to the method in 1, and obtain the colon-targeted acid-base and bacterial flora sensitive capsule for oral administration.

Figure 1:
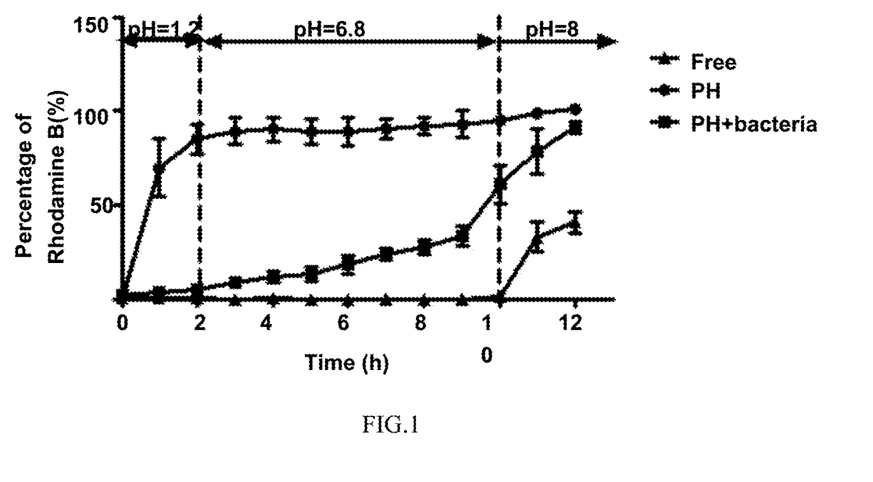
FIG. 1 is a diagram of capsule release curves in simulated gastric juice, small intestinal juice and colon juice in vitro in embodiment 1 of the present invention.
Figure 2:
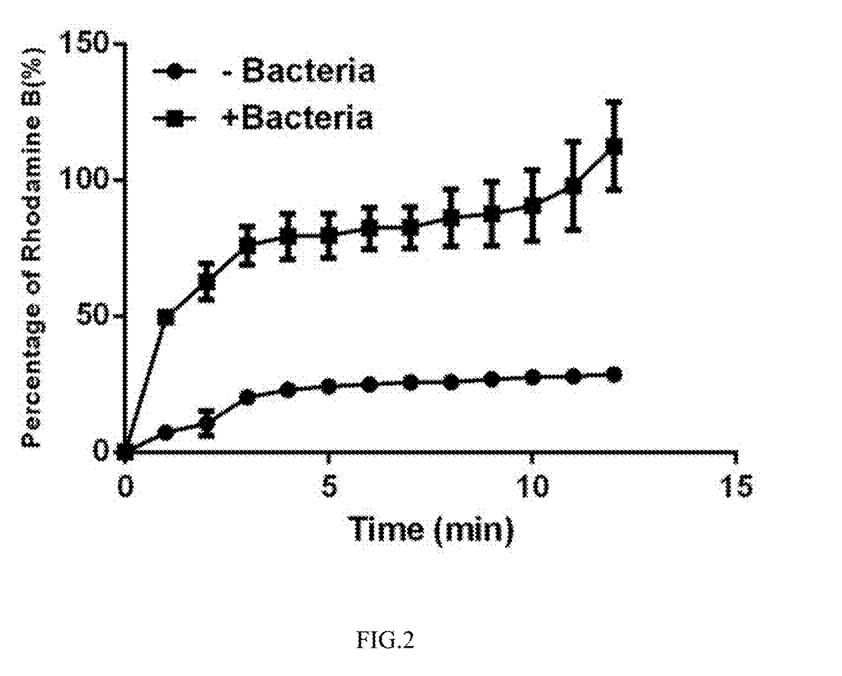
FIG. 2 is a diagram of release curves of the bacterial flora sensitive layer in non-aseptic and aseptic simulated colon fluid in embodiment 1 of the present invention.

Carry out in vitro investigation on the dissolution and release of the acid-base and bacterial flora sensitive capsule by the simulated gastrointestinal juice, and the result is shown in FIG. 1. It can be seen from FIG. 1 that ordinary capsules with dyes are dissolved and released completely in the environment of pH=1.2, the single pH sensitive layer is partially released in the simulated intestinal juice at pH=6.8 after withstanding acidic conditions, and the acid-base and bacterial flora sensitive layer capsule are not released until it withstands the simulated gastric juice and small intestinal juice and reaches the colon juice. Subsequently, the specificity of sensitivity to bacterial flora is investigated. The results of capsule release in non-aseptic and aseptic simulated colon juice are shown in FIG. 2, the capsule is quickly released under the non-aseptic codition while shows incomplete release under the aseptic codition, so the specificity of the bacterial flora sensitive layer is proved.

3. Preparation of Targeted Nanoparticles

Prepare CD-98 antibody modified PLGA-PEG nanoparticles by the double emulsion method. Dissolve drugs or imaging reagents in the aqueous phase, and dissolve 20±10 mg PLGA-PEG in dichloromethane (DCM) (J&K, China). After ultrasonic processing into emulsion, add into aqueous phase containing 1.5±1% Tween −80 for secondary phacoemulsification. After stirring and volatilization for 2.5±1 h, carry out ultrafiltration with a supercentrifugation tube, wash with water for three times, obtain the nanoparticles, and freeze dry for standby application.

Add PEG end —COOH activated by NHS and EDC, add CD-98 antibody for incubation, obtain the modified CD-98 antibody nanoparticles, and freeze dry for standby application.

4. Preparation of Oral Colon-Targeted Delivery System

Dissolve β-cyclodextrin polymer crosslinked with epichlorohydrin or plant fiber extract in dimethyl sulfoxide. Draw a proper amount of the solution into the mould gelatin capsule shell, and then dry at high temperature. After cooling to room temperature, the capsule intermediate layer sensitive to colon bacterial flora is obtained.

After clamping the capsule shell sensitive to colon bacterial flora vertically, mix Eudragit S100, triethyl citrate and talc powder to form the coating fluid of the pH sensitive layer, stir and mix evenly. Spray the coating fluid outside the capsule evenly by the coating pan, and obtain the double-sensitive oral capsule with the pH sensitive layer as the outer layer and the bacterial flora sensitive layer as the intermediate layer.

Figure 3:
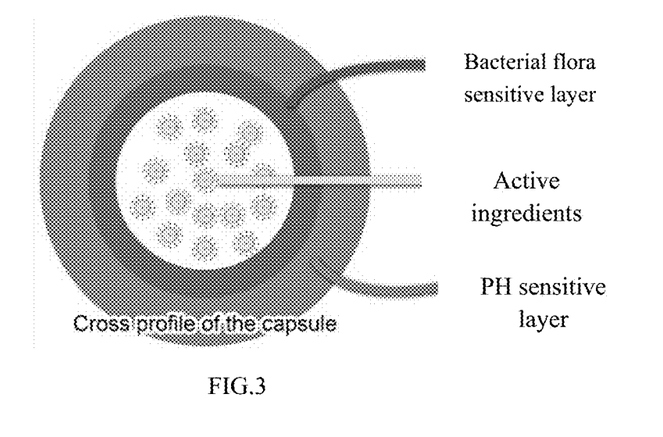
FIG. 3 is a structure diagram of the oral colon-targeted delivery system of the present invention.

Add the drug-loaded targeted nanoparticles prepared in the above 3 into the double-sensitive oral capsule, and obtain the oral colon-targeted delivery system of the present invention. The structure of the oral colon-targeted delivery system is shown in FIG. 3, the outer layer is the pH sensitive layer which is dissolved only at pH≥8 and can resist the acidic environment at the middle and upper ends of the stomach and small intestine; the middle layer is the bacterial flora sensitive layer which can only be dissolved when triggered by the bacterial flora specific to the colon site and can effectively enhance the selective delivery capability of the delivery system to the colon site; The active ingredients in the inner layer are drug-loaded targeted nanoparticles, which can be specifically identified and enriched at the inflammatory site, stay for a long-lasting effect, release drugs slowly, reduce the number of times of administration, and enhance the therapeutic effect on the site of colon lesion.

Embodiment 2 Characterization of Targeted Nanoparticles and Drug Release In Vitro 1. Measurement of Targeted Nanoparticle Size and Surface Zeta Potential To measure the particle size and zeta potential of nanoparticles and targeted nanoparticles by dynamic light scattering, draw 1 mL solution sample, add into the sample cell, make sure there is no bubble generated in the container, measure the particle size and zeta potential of the samples with the MALVERN nanometer particle size measuring instrument (DLC), measure each sample repeatedly for three times, and obtain the particle size and potential. Observe the samples with an electron microscopy (TEM).

Figure 4:
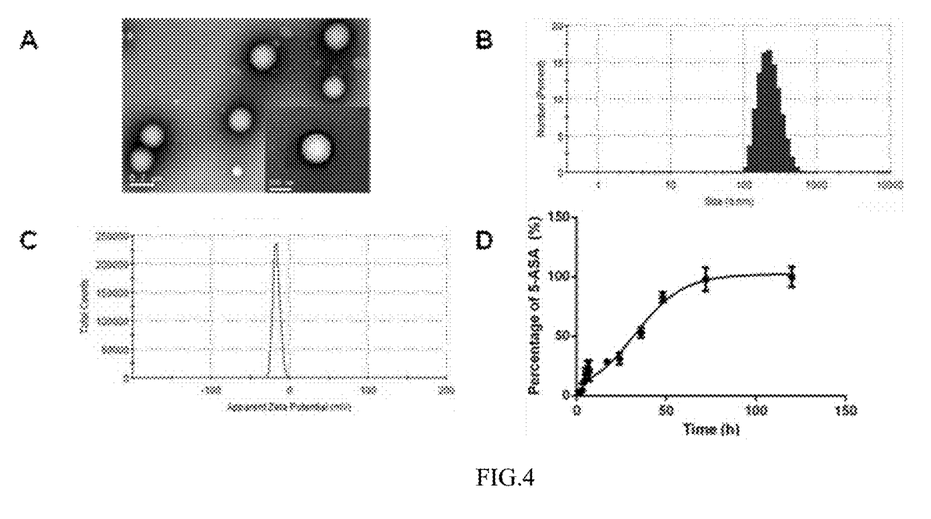
FIG. 4 is a diagram of curves for characterization of targeted nanoparticles and their drug release in vitro in embodiment 2 of the present invention.

The result of dynamic light scattering shows that (see Table 1) the nanoparticle size is about 143.1 nm, and the ζ potential is about −27.9 mv. As shown in FIG. 4, the analysis of NP-CD98 shows that the average particle size according to TEM evaluation is about 200 nm in FIG. 4A but about 224.9 nm in FIG. 4B according to DLC evaluation. Because TEM technology requires particles drying in vacuum, this will lead to particle contraction. FIG. 4C shows that the ζ potential of nanoparticles is −16.8±0.452 mV. The size is increased by about 80 nm, the ζ potential also changes greatly, both facts show that the NP antibody is bound to the CD98 antibody successfully.

TABLE 1

Size and Charge Distribution of Nanoparticles and Targeted Nanoparticles

|  | PDI | SIZE (nm) | ZETA (mv) |
| --- | --- | --- | --- |
| NP | 0.219 ± 0.030 | 143.1 ± 4.073 | −27.9 ± 0.379 |
| NP-CD98 | 0.245 ± 0.067 | 224.9 ± 8.965 | −16.8 ± 0.452 |

2. Drug Release

The targeted nanoparticles are released in vitro in phosphate buffer (PBS, pH6.8). Nanoparticles with the concentration of 0.02 mg/ml are suspended in a microdialyzer (Thermo Fisher, USA) and incubated in a shaking table at the speed of 100 rpm at 37° C. Take out 100 ul from each of the three tubes, add 100 ul PBS (pH=7.4, 0.01M) (Gibio, USA) to supplement the volume and balance the system at each designated point of time (0, 1, 2, 3, 4, . . . 0.12, 24 and 48 hours). Measure the 5-ASA drug content in PBS with a NanoDrop 2000 UV-Vis spectrophotometer, and fit into a curve.

The result is shown in FIG. 4D. PBS with pH 7.4 is used as the release medium to provide a good sink condition, NP-CD98 presents a slow release curve, and more than 80% is released only after incubation for 48 h. This allows sustained release of the drugs at the inflammatory site of IBD.

Embodiment 3 Targeting Experiment of Nanoparticles

1. Cell Uptake

Culture RAW 264.7 macrophages in a culture dish overnight. Replace the culture medium with a serum-free medium containing NP and NP-CD98. After incubation for 3 hours, rinse RAW264.7 macrophages with PBS (pH value=7.4) thoroughly to remove excessive nanoparticles, and then fix with 4% polyformaldehyde for 20 minutes. After dilution of 6-diamidino-2-phenylindole dihydrochloride (DAPI) by 10,000 times, dye the cell nucleus for 5 minutes, and observe the cell uptake of nanoparticles under laser confocal microscopy.

2. Quantitative Cell Uptake of Nanoparticles

Inoculate RAW 264.7 macrophages in a 6-well plate. After incubation with NP and NP-CD98 for 2 hours, to remove free nanoparticles, wash with PBS for 3 times, disperse the cells, centrifugate (1000 revolutions, 10 minutes), and redisperse to the concentration of 1×10$^6$ cells/lml. Measure the cell fluorescence uptake with Accuri C6 flow cytometer (Becton Dickinson, California).

Figure 5:
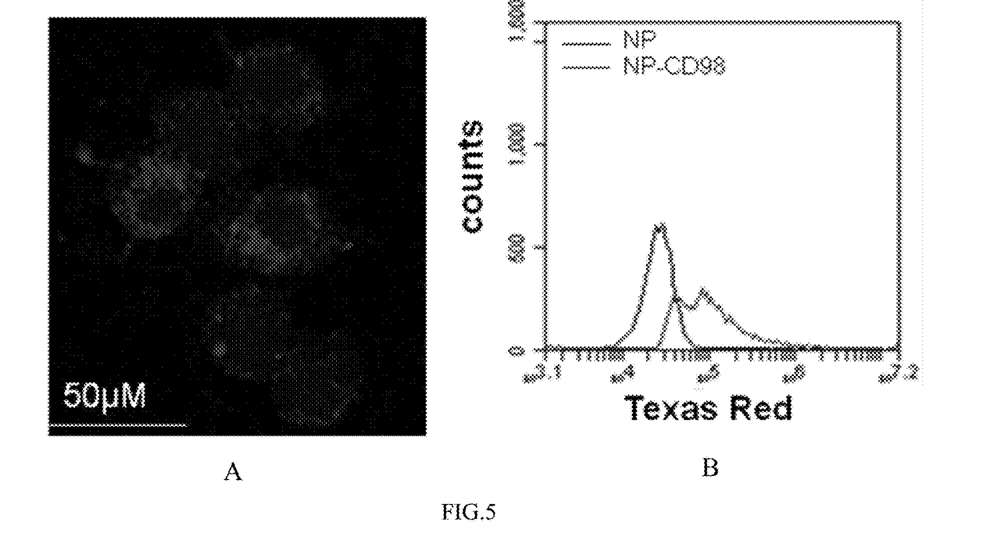
FIG. 5 is a diagram of nanoparticles targeting experiment results in embodiment 3 of the present invention.

The results are shown in FIG. 5. It can be seen from FIG. 5A that endocytosis of nanoparticles with red fluorescence light is possible. The black lines in FIG. 5B represent the nanoparticles, and the red lines represent the targeted nanoparticles. It can be observed that the red lines move to the right more obviously than the black lines, which indicates that the fluorescence signal produced by the targeted nanoparticles is obviously higher than that produced by the nanoparticles, that is, the targeted nanoparticles have obvious targetability. In FIG. 5, A. laser confocal diagram of endocytosis of nanoparticles; B. Flow layout of NP and NP-CD98 endocytosis.

Embodiment 4 Distribution of Capsules in Gastrointestinal Tract

1. In Vivo Imaging

Prepare the fluorescent capsules by adding Rhodamine B (30 mg/ml) into the pH and bacterial flora double-sensitive (pH+bacteria) capsules, and then give intragastric administration to rats. Divide the rats into three groups. Put them to death in 3 hours, 6 hours and 12 hours. Take the whole gastrointestinal tract, including the stomach, small intestine (SI-1, SI-2, SI-3) and colon part, observe and analyze the image by the Kodak IS ex vivo FX imaging system. $E_x$=535 nm at $E_M$=600 nm.

Figure 6:
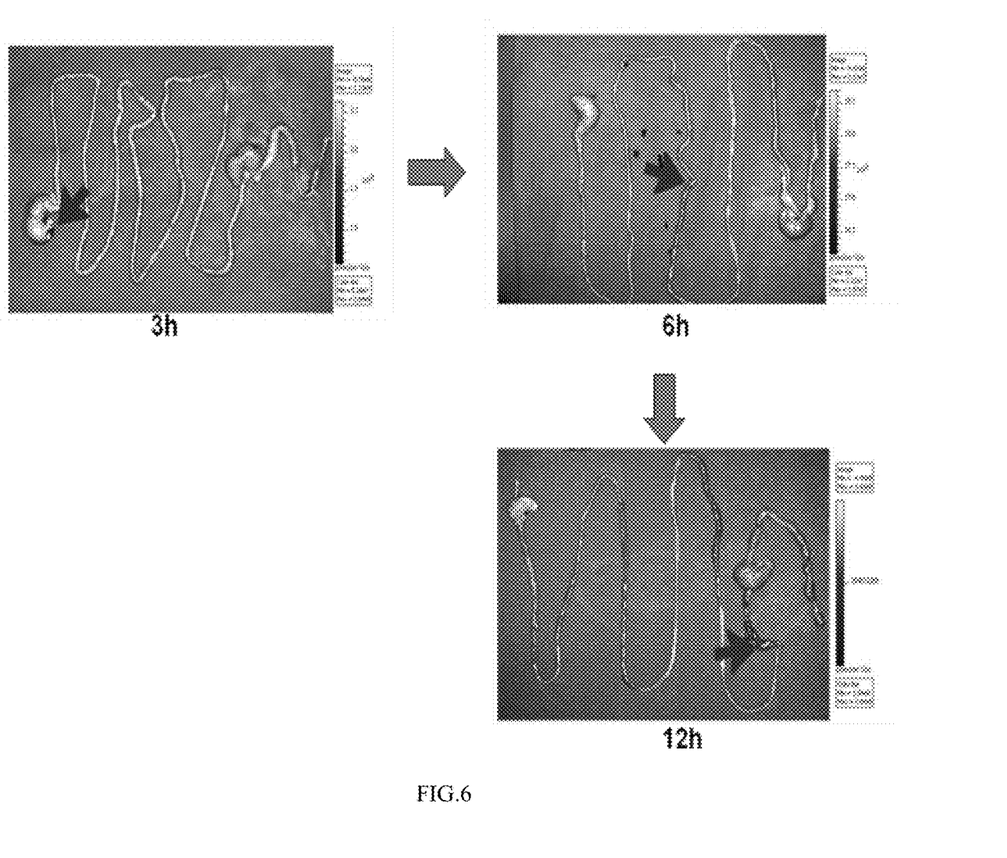
FIG. 6 is a diagram of distribution of capsules sensitive to both pH and bacterial flora in vivo in embodiment 4 of the present invention.

The result is shown in FIG. 6. It can be seen from FIG. 6 that capsule-shaped fluorescence appears in the stomach 3 hours after intragastric administration, and appears in the middle part of the small intestine in 6 hours. The complete capsule appears in the site at the distal end of the small intestine close to the cecum in 12 hours, and this illustrates that the pH and bacterial flora double-sensitive capsules of the present invention maintain their integrity when going through the gastrointestinal tract.

2. Biodistribution

Give intragastric administration to the rats with ordinary capsules, pH-sensitive capsules and TEXAS RED pH+bacteria capsules respectively, and put them to death in 18 hours. Take the whole gastrointestinal tract and divide it into four parts, including stomach, SI-1, SI-2, SI-3 and colon. Then cut into slices with a freezing microtome, and observe the specific distribution of fluorescent light under a confocal laser scanning microscope. Homogenize tissue samples in PBS, and then extract with a mixture of ethanol/DMSO (1:1 volume/volume). Analyze the fluorescent light content in the samples with a fluorescent plate reader.

Figure 7:
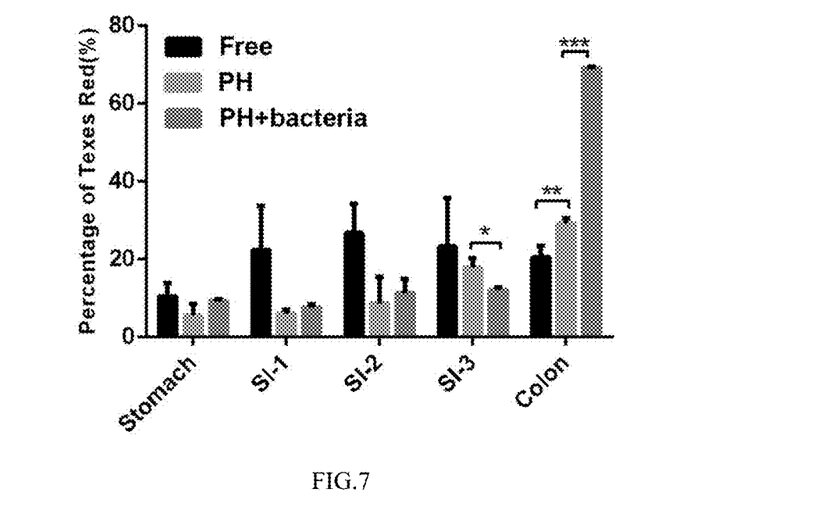
FIG. 7 is a columnar comparison diagram of capsules distribution in vivo in embodiment 4 of the present invention.

The result is shown in FIG. 7, obvious red fluorescence light appears in all five segments of the ordinary capsule, which indicates that it does not have any protective effect. For the single pH sensitive layer, fluorescent light appears only at the lower end of the small intestine and at the colon site. For the pH and bacterial flora double-layer sensitive capsule of the present invention, fluorescent light appears only at the colon site, which is consistent with the statistical data. This fully illustrates that the double-layer sensitive capsule of the present invention has a good colon targeting effect in vivo.

Embodiment 5 Investigation into Retention Time of Nanoparticles at the Colon Site Put free dyes, NP and NP-CD98 in pH+bacteria capsules respectively, give intragastric administration to rats, put them to death in 18H, 24H and 30H, and take the colon site. Dye the cell nucleus with DAPI. More details of Texas Red in the tissues can be observed by laser confocal microscopy. Homogenize the tissue samples in PBS, and then extract with the mixture of ethanol/DMSO (1:1 volume/volume). Analyze the fluorescent light content in the samples with the fluorescent plate reader.

Figure 8:
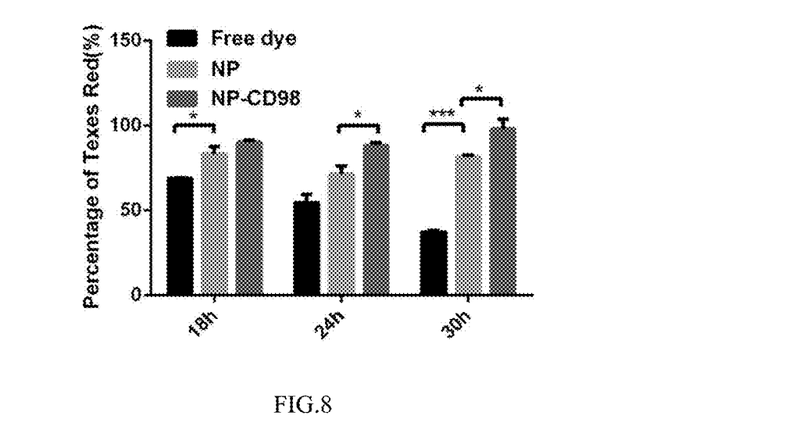
FIG. 8 is a bar chart of statistical data of colon site fluorescence when nanoparticles are accumulated at the colon site for 18 h, 24 h and 30 h in embodiment 5 of the present invention.

The result is shown in FIG. 8. In the free dye group, the fluorescence intensity is decreased significantly during 18 to 30 hours, which indicates that the retention time is short. The targeted nanogroup has significantly higher fluorescence intensity and smaller change than those of the nanogroup, which indicates that most targeted nanoparticles enter the colon tissue for sustained release so that the time is prolonged.

Embodiment 6 Drug Efficacy Experiment In Vivo

1. Ordinary Capsules Encapsulating Free Drugs, pH-Sensitive Capsules Encapsulating Free Drugs and PH+Bacteria-Sensitive Capsules Encapsulating Drug-Loaded NP-CD98 are Intragastrically Administered Investigate the drug efficacy in vivo with a DSS-induced acute enteritis model. Divide rats (about 150 g) into 5 groups, with 10 rats in each group. Except the first group as the negative control group, provide free drinking of dextran sulfate sodium (DSS) (6.5%) for 10 days for other groups respectively. Take the second group as the positive control group, intragastrically administer other groups with the free drugs encapsulated with ordinary capsules, free drugs protected by the pH layers and capsules protected by the double sensitive layer of pH+bacteria with NP-CD98 encapsulated drugs every other day. Weigh the rats on a daily basis, and count the number of dead rats. After 10 days, kill all the rats, and take out the colon and spleen. Measure the length of the colon site, and weigh the spleen.

2. MPO Activity

Quantify the neutrophil infiltration by measuring the MPO activity. Measure with Sigma's myeloperoxidase kit. MPO activity is expressed as a protein unit per milligram, and one unit is defined as the amount of 1 millimole degraded into hydrogen peroxide per minute at 25° C.

3. Results

Figure 9:
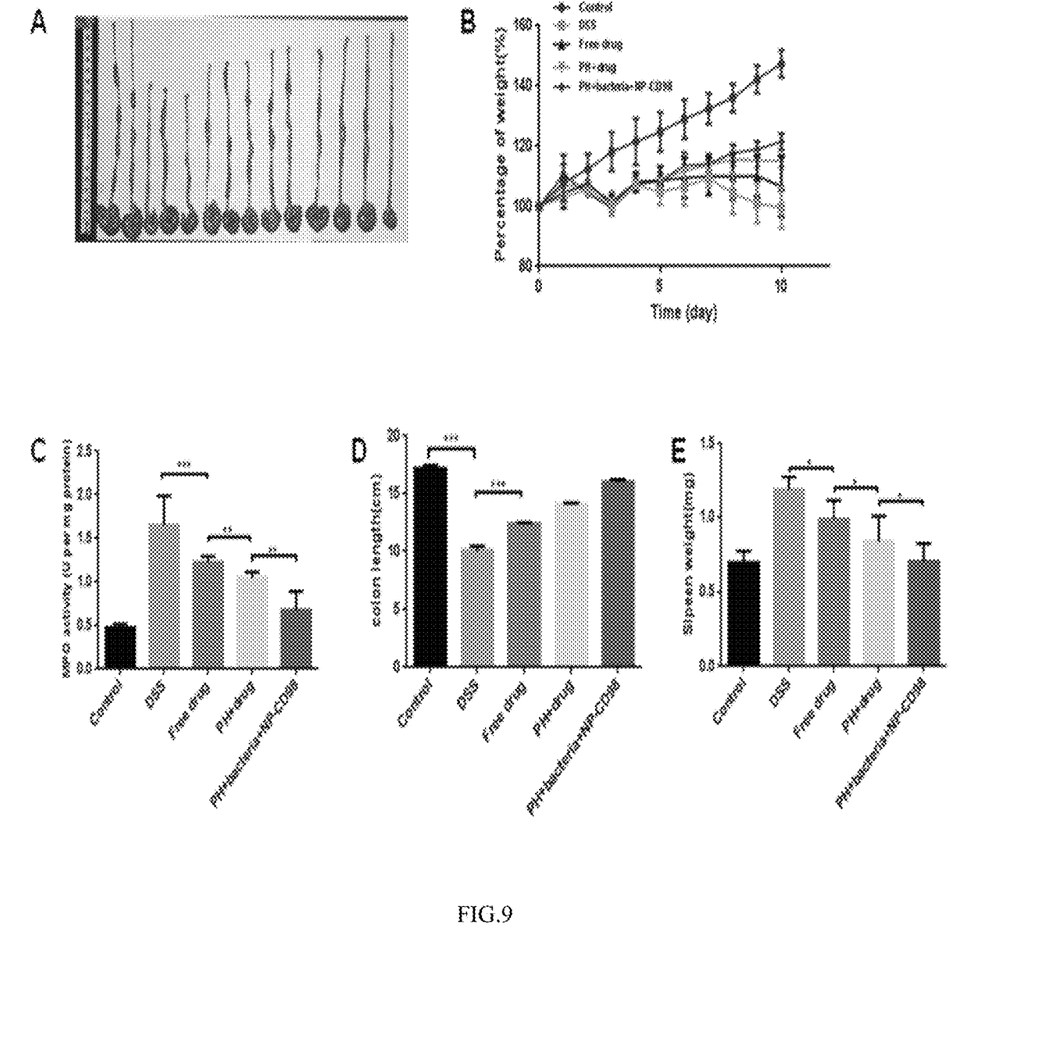
FIG. 9 is a diagram of therapeutic results of ordinary capsules, pH sensitive capsules encapsulating free drugs and PH and bacterial flora sensitive capsules encapsulating NP-CD98 on DSS-induced rat disease models in embodiment 6 of the present invention.

As shown in FIG. 9 (in FIG. 9, A. Colon diagram, B. Body weight change of rats, C. MPO value, D. Colon length, E. Spleen weight), the body weight of rats processed with DSS began to differ on the 4th day, and the difference was the greatest on the 10th day. Among the three groups, the PH+bacteria sensitive capsules encapsulating NP-CD98 has the minimum weight loss (as shown in FIG. 9B). Better therapeutic effects are shown from both reduction of colon length (shown in 9D) and increase of spleen weight (shown in 9E). The results in FIG. 9C show that MPO activity is consistent with the results of colon length and spleen weight. These results reflect that the PH+bacteria sensitive capsule group encapsulating NP-CD98 achieves a better effect and significantly reduces the inflammation of the colon.

The above-mentioned embodiments only express the implementation of the present invention, which are described in a more specific and detailed manner but cannot be construed as restrictions on the scope of the present patent for invention. It should be pointed out that several transformations and improvements can also be made for one of ordinary skill in the art without departing from the concept of the present invention, and all of them fall into the scope of protection intended to be provided by the present invention. Therefore, the scope of protection of the present patent for invention shall be determined based upon the appended claims.

The invention claimed is:

1. An oral colon-targeted delivery system comprising:
   a bacterial flora sensitive layer which contains polysaccharides and covers an active ingredient, wherein the active ingredient comprises a drug and/or a diagnostic reagent in a nanoparticle dosage form, wherein the polysaccharides comprise β-cyclodextrin polymer crosslinked with epichlorohydrin; and
   a pH sensitive layer which contains a polymer composition dissolved under the condition of pH≥7 and covers the exterior of the bacterial flora sensitive layer, wherein the pH-sensitive layer is the outermost layer of the oral colon-targeted delivery system.

2. The oral colon-targeted delivery system according to claim 1, wherein the polymer composition of the pH sensitive layer comprises components of the following weight percentages: 10%~43% of methacrylic acid-methyl methacrylate copolymer, 5%~36% of plasticizer and 5%~22% of talcum powder, based on the total weight of the pH sensitive layer.

3. The oral colon-targeted delivery system according to claim 1, wherein the dosage form of the delivery system comprises capsules, microcapsules, tablets, pills or granules.

4. The oral colon-targeted delivery system according to claim 1, wherein the drug comprises a protein drug, antibody drug, or gene drug.

5. The oral colon-targeted delivery system according to claim 1, wherein the diagnostic reagent comprises an imaging reagent.

6. The oral colon-targeted delivery system according to claim 1, wherein the nanoparticle is in a targeted nanoparticle dosage form.

7. The oral colon-targeted delivery system according to claim 6, wherein the nanoparticle comprises a PLGA-PEG nanoparticle modified by CD-98 antibody.

8. The oral colon-targeted delivery system according to claim 3, wherein the preparation method of the delivery system of the capsule dosage form comprises the following steps:

dissolving polysaccharides in an organic solvent to obtain a solution, drawing a proper amount of the solution, adding into a capsule shell, drying at 45~65° C. for 5~15 hours, then cooling to room temperature, and obtaining the bacterial flora sensitive layer; and preparing a coating fluid of the pH sensitive layer by mixing the polymer compositions dissolved under the condition of pH≥7, spraying on the outer surface of a capsule shell containing the bacterial flora sensitive layer, and obtaining the oral colon-targeted delivery system sensitive to both pH and bacterial flora after drying.

* * * * *